United States Patent [19]

Khait et al.

[11] Patent Number: 4,940,939
[45] Date of Patent: Jul. 10, 1990

[54] APPARATUS WITH INDUCTIVE LOOP SYNCHRONIZED OSCILLATORS FOR MEASURING THE MAGNETIC CONTENT OF NON-METALLIC SAMPLES

[76] Inventors: Alexandr L. Khait, prospekt; Kultury, 17, kv. 8; Boris A. Glagovsky, prospekt Morisa Toreza, 15, kv. 49; Larisa R. Frenkel, ulitsa Butlerova, 8, kv. 101, all of Leningrad; Vera S. Los, ulitsa Komsomolskaya, 21, kv. 24, Sosnovy Bor, all of U.S.S.R.

[21] Appl. No.: 321,014

[22] Filed: Mar. 9, 1989

[51] Int. Cl.⁵ ............... G01R 33/12; G01N 27/72; H03B 27/00
[52] U.S. Cl. .................................. 324/236; 324/233; 331/55
[58] Field of Search ............... 324/233, 234, 236, 237, 324/238, 327, 328, 377; 331/55, 56, 64, 65

[56] References Cited

U.S. PATENT DOCUMENTS 3,146,405  8/1964  Talmasky et al. ............ 331/56
3,492,564  1/1970  Baker, Jr. ................ 324/328 X
3,808,524  4/1974  Tarassoff .
3,875,498  4/1975  Mahan et al. .............. 324/328

OTHER PUBLICATIONS

Glagovsky et al., "Kontrolno-Izmeritelnye Pribory I Osnovy Avtomatizatii Proizvodstva Abrazivnykh Instrumentov", Mashinostroenie Leningrad, 1980, pp. 126, 127.

Primary Examiner—Gerard R. Strecker
Attorney, Agent, or Firm—Lilling & Greenspan

[57] ABSTRACT

An apparatus for measuring the magnetic content of non-metallic samples includes operating and reference sine wave oscillators of identical frequency, a mutual synchronization loop for said oscillators, and a phase meter connected to the oscillator outputs for measuring the phase shift between their oscillations, when a test sample is placed inside the inductance coil of the operating oscillator. The mutual synchronization loop includes a switchable resistive attenuator for varying the resistance of the mutual synchronization loop according to the magnetic content of the test sample, such that the phase shift between the oscillations of the oscillators, with any value of content within the specified measuring range, is not in excess of 30 deg.

2 Claims, 2 Drawing Sheets

APPARATUS WITH INDUCTIVE LOOP SYNCHRONIZED OSCILLATORS FOR MEASURING THE MAGNETIC CONTENT OF NON-METALLIC SAMPLES

BACKGROUND OF THE INVENTION

1. Field of the Invention

The present invention relates to checking the composition of non-metallic materials and, more particularly, to apparatus for measuring the magnetic content of non-metallic samples. The invention can be used in manufacture of abrasive materials, construction materials, electric-grade and radioceramics, and in production of foodstuffs such as flour and sugar.

2. Description of the Prior Art

Known in the prior art is an apparatus for determining the amount of magnetic material in a sample (U.S. Pat. No. 3,808,524) comprising a measuring frequency oscillator with the test sample placed within the coil, a reference frequency oscillator, a mixer having its inputs connected to the outputs of the oscillators and its ouput connected, through a low-pass filter, to the input of a frequency-to-voltage converter whose output is connected to an analog or digital voltmeter. The magnetic content of the sample is determined by the frequency difference between the measuring frequency oscillator and the reference frequency oscillator, after the test sample has been placed inside the coil of the measuring frequency oscillator.

This apparatus has a low sensitivity, preventing the check to be performed on test samples with a magnetic content of below 0.1%. The low sensitivity of the apparatus is due to the fact that the placement of a low magnetic content sample within the measuring frequency oscillator coil may fail to result in a frequency change of the measuring frequency oscillator because of the spurious coupling tending to exist between this oscillator and the reference frequency oscillator. In addition, the sensitivity of the apparatus is limited by the available frequency stability of the two oscillators.

An apparatus is known for measuring the magnetic content of non-magnetic samples, which comprises a pair of identical self-excited sine wave oscillators, namely, the operating and reference frequency oscillators, coupled by a mutually synchronizing circuit, and a dual-channel phase meter connected to the oscillator outputs (B. A. Glagovsky et al. "Kontrolno-izmeritelnye pribory i osnovy avtomatizatsii proizvodstva abrazivnykh instrumentov", Mashinostroenie, Leningrad, 1980, p. 126–127). The test sample is placed in the inductance coil of the resonant circuit of the operating oscillator, leading to a change in the tuning frequency of the resonant circuit. Since both the operating and the reference frequency oscillators are mutually synchronized, the oscillation frequency of the operating oscillator is not changed. Instead, a phase shift is generated between the oscillator waves which is measured by a phase meter. The value $\phi$ of the phase shift is given by:

$$\phi = \pm \arcsin\left(\frac{E_m}{E} KP\right), \tag{1}$$

wherein $E_m$ is the amplitude of oscillations in the resonant circuit of the operating oscillator, E is the amplitude of synchronizing oscillations applied to the resonant circuit of the operating oscillator from the reference frequency oscillator through the mutualy synchronizing circuit, K is the proportionality coefficient dependent on the properties of the material to be tested and on the inductance coil parameters in the resonant circiut of the operating oscillator, and P is the magnetic content of the test sample.

The $E_m/E$ ratio, which is the coupling coefficient between the resonant circuits of the oscillators, depends on the resistance of the mutual synchronization loop. In this apparatus, the mutual synchronization loop is fixed, i.e. it has a constant coupling coefficient.

The coupling coefficient value is chosen so that the phase shift between the oscillations of the operating and reference frequency oscillators, for a specified magnetic content measurement range, will not exceed 90°. If the phase shift between the oscillator waves is in excess of 90°, the mutual synchronization mode is disturbed.

The above expression shows that the phase angle between the oscillations of the two oscillators is a nonlinear function of the magnetic content P of the test sample, resulting in a measurement error. This error signal is comparatively insignificant on the initial portion of the curve plotted using the above expression, i.e. with small amounts of magnetic materials, but an abrupt rise occurs as the amount is increased. In actual devices of the type described, the upper limit of the measurement range with an acceptable error is only 0.1%, whereas the magnetic inclusion content of, say, abrasive materials may be as large as 3%. Thus the accuracy of the apparatus as described above is reduced as the value to be measured increases.

SUMMARY OF THE INVENTION

It is an object of the present invention to increase the accuracy of the apparatus for measuring the magnetic content of non-metallic samples.

Another object of the present invention it to extend the measuring range for the magnetic content of non-metallic samples towards higher values by reducing, for these higher values, the error due to the nonlinear relationship between the phase angle formed by the sine waves of two mutually synchronized oscillators, with the test sample placed within the coil of one of them, and the magnetic content of this sample.

With these and other objects in views, there is provided an apparatus for measuring the magnetic content of non-metallic samples, comprising an operating sine wave oscillator including an inductance coil adapted to receive the test sample, a reference sine wave oscillator with its frequency equal to that of the operating oscillator, a mutual synchronization loop for said oscillators, and a phase meter connected to the outputs of the oscillators for measuring the phase shifter betwen their oscillations as the test sample is placed within the coil of the operating oscillator. The mutual synchronization loop includes a variable resistive attenuator for varying the mutual synchronization loop resistance as a function of the magnetic content of the test sample, so that the phase shift between the oscillations of the operating and reference oscillators, with any amount of the magnetic materials in test sample within a specified measurement range, will not be in excess of 30°.

In the proposed apparatus, an increased accuracy of measurement for upper limits of magnetic content within a specified range is achieved by incorporating a variable resistive attentuator, allowing of the specified measuring range into a number of subranges assigned each to the specific attentuator setting i.e. to the specific resistance of the mutual synchronization loop of both the operating and reference oscillators. The values of the attenuator resistors are chosen so that the phase angle between the waves of the operating and reference oscillators, within each of these subranges, does not exceed 30°, and the measurement error due to the non-linear relationship of said phase angle and the magnetic content is correspondingly reduced.

It is advisable that the operating and reference oscillators each include an operational amplifier with its non-inverting input connected to the output through a capacitor, and that the resonant circuit of each of these oscillators be connected to the inputs of the respective operational amplifier.

Such an oscillator circuit provides an increased stability of its oscillation frequency, thus reducing the additive measuring error that would result in a smaller measurement accuracy for the lower values of the measured amount within a specified range.

These and other objects and advantages of the invention will be more apparent from the following detailed description of its preferred embodiment, with reference to the accompanying drawings.

DESCRIPTION OF THE PREFERRED EMBODIMENT OF THE INVENTION

Figure 1:
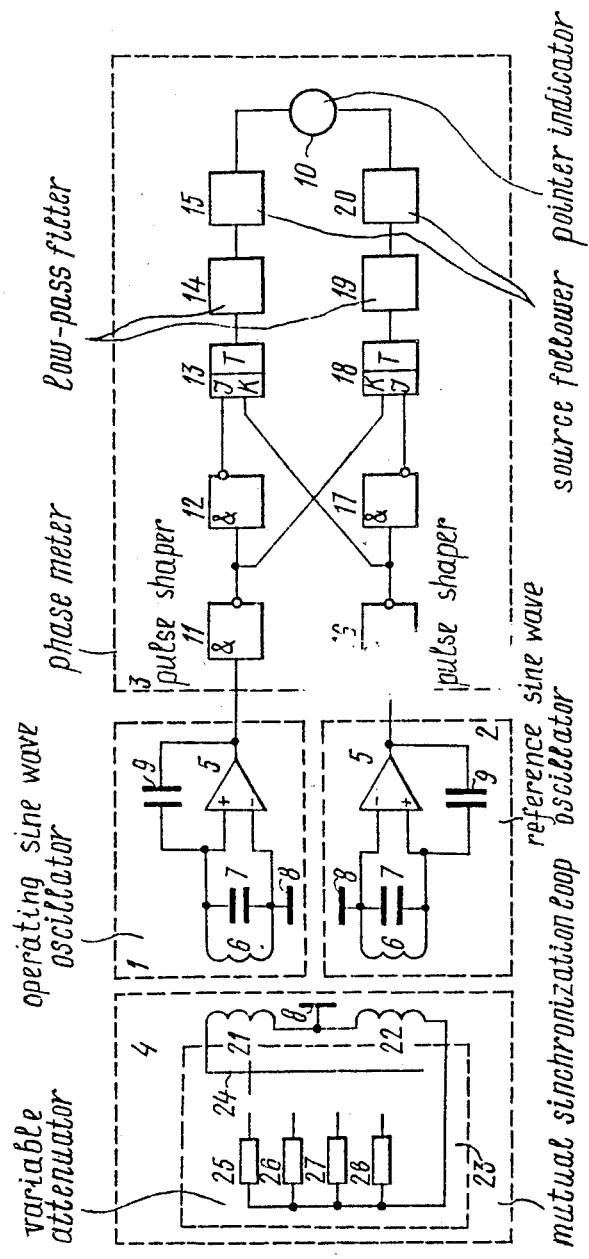
FIG. 1 represents the block diagram of an apparatus for measuring the magnetic content of non-metallic samples, according to the invention.

The apparatus for measuring the magnetic content of non-metallic samples comprises an operating sine wave oscillator 1 (FIG. 1), a reference sine wave oscillator 2, a phase meter 3, and a mutual synchronization loop 4 for the oscillators 1 and 2. The oscillators 1 and 2 are LC-oscillators based on identical elements. The oscillators 1 and 2 each include an operational amplifier 5 with a resonant circuit connected between its non-inverting and inverting inputs, the resonant circuit consisting of an inductance coil 6 and a capacitor 7. The resonant circuits of the operating oscillator 1 and the reference oscillator 2 have the same tuning frequency. The inductance coil 6 of the oscillator 1 is adapted to receive the test sample. The inverting input of each operational amplifier 5 is connected to a common bus 8 of the apparatus. Connected between the non-inverting input of each operational amplifier 5 and its output is a capacitor 9. It is the output of the respective operational amplifier 5 that serves as the output of each of the oscillators 1 and 2.

The circuit configuration of the oscillators 1 and 2 disclosed herein is to be preferred, since it provides a high frequency stability owing to the performance stability of the operational amplifier and the minimum number of elements in the resonant circuit. The high frequency stability of the oscillators 1 and 2 results in a lower additive measurement error, which contributes to extending the measuring range into the region of small values of the measured amount wherein the measurement result might be comparable to this error. On the other hand, if there is no need to measure the small values of the magnetic content, e.g. on the order of thousandths per cent, other configurations of the operating and reference oscillators can be used, such as the three-point circuits.

The phase meter 3 comprises two identical channels and an indicator, such as a pointer indicator 10. The first channel of the phase meter 3 includes a pulse shaper 11, an inverter 12, a JK-flip-flop 13, a low-pass filter 14, and a source follower 15, whereas the second channel includes a pulse shaper 16, an inverter 17, a JK-flip-flop 18, a low-pass filter 19, and a source follower 20. The pulse shapers 11 and 16 are designed to convert sine wave oscillations into square-pulse sequences, the pulse width being equal to half the sine wave period. The pulse shapers 11 and 16 may be formed by NAND gates.

The inputs of the pulse shapers 11 and 16 serve as the inputs of the phase meter 3 and are connected to the outputs of the oscillators 1 and 2, respectively. The output of the pulse shaper 11 is connected to the K-input of the flip-flop 18 and, through the inverter 12, to the J-input of the flip-flop 13. The output of the pulse shaper 16 is connected to the K-input of the flip-flop 13 and, through the inverter 17, to the J-input of the flip-flop 18. The direct outputs of the flip-flops 13 and 18 are connected through the low-pass filters 14 and 19, respectively, to the inputs of the source followers 15 and 20, respectively, which act as power amplifiers. The outputs of the source followers 15 and 20 are connected to the pointer indicator 10 with its scale calibrated in measuring units of content, i.e. in %.

According to the invention, the mutual synchronization loop 4 of the oscillators 1 and 2 comprises two identical inductance coils 21 and 22 and a variable attenuator 23 consisting of a switch 24 and a number, four in this example, of resistors 25, 26, 27 and 28. The coil 21 is inductively coupled with the coil 6 of the operating oscillator 1, and the coil 22 is inductively coupled with the coil 6 of the reference frequency oscillator 2. The first terminals of the inductance coils 21 and 22 are connected to each other and to the common bus 8 of the apparatus. The second terminal of the coil 21 is connected to the transfer contact of the switch 24, and the second terminal of the coil 22 is connected to the first terminals of the resistors 25, 26, 27 and 28. The second terminal of each of the resistors 25, 26, 27 and 28 is connected to the respective transferred contact of the switch 24.

The number of adjustable steps of the attenuator 23, and consequently, the number of component resistors making up the attenuator 23 is dependent on the specified measurement range and the accuracy required. The wider the range of measurement and the higher the accuracy required, the greater the number of resistors needed for the attenuator 23. The attenuator 23 serves to divide the specified measurement range into a number of subranges, a specific resistance value of the mutual synchronization loop 4, i.e. a specific value of the coupling coefficient $E_m/E$ in Eq. (1) being assigned to each of the subranges. For example, the specified measurement range from 0 to 3% may be split into the following subranges: from 0 to 0.1%, from 0 to 0.3%, from 0 to 1%, and from 0 to 3%, the resistance ratio of the resistors 25 to 28 being 3:1:0.3:0.1. Therefore, the measurements can be made in different subranges according to the value of the measured quantity, the measurement error for upper values of the measured quantity, within the specified range, being substantially reduced by an appropriate choice of resistances of the resistors 25 through 28. For most present-day industries, the allowable manufacturing error, generally, does not exceed 10%. As shown by calculations, such measuring accuracy is attained by providing that the values of the resistors 25 through 28 should be selected so that the phase shift between the oscillations of the operating oscillator 1 and the reference oscillator 2, at the upper end of each measuring subrange, is not in excess of 30 deg.

The configuration of the attenuator may differ from that shown in FIG. 1, provided that the above requirements for selection of the resistor values of the attenuator are met.

The operation of the apparatus is further illustrated by FIGS. 2a through 2k showing, on the left, the electric outputs of the elements of the apparatus with no test sample placed in the coil 6 of the operating oscillator 1, and on the right the outputs of the same elements with the test sample placed within the coil 6 of the oscillator 1.

Figure 2:
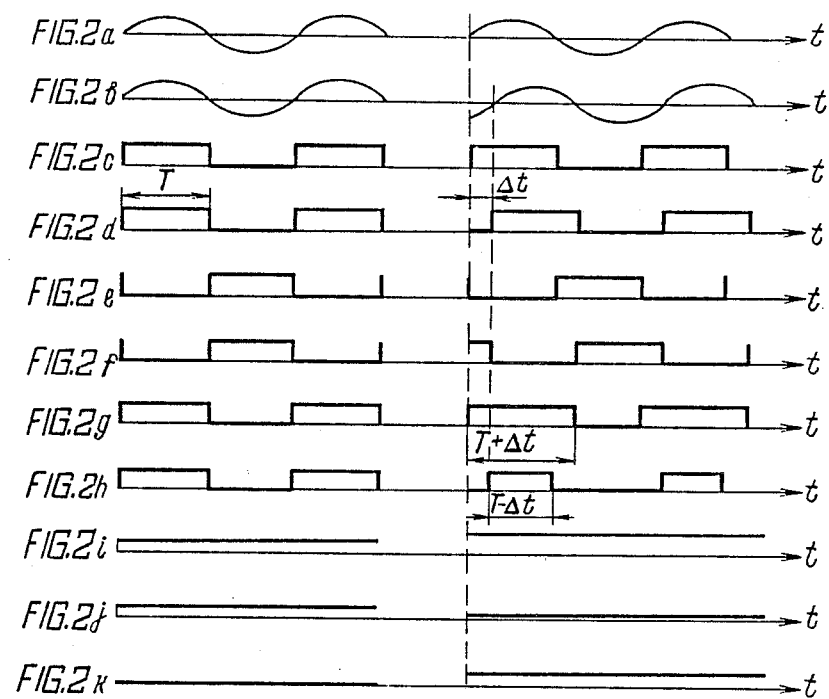
FIGS. 2a–2k are timing signal diagrams illustrating the operation of the apparatus shown in FIG. 1.

The oscillators 1 and 2 generate sine waves of identical amplitude and frequency, shown in FIGS. 2a and 2b, respectively. The phase shift between the waves of the oscillators 1 and 2, with no test sample placed inside the coil 6 of the oscillator 1, is equal to zero. These oscillations drive the inputs of the shapers 11 and 16 to give square pulses at the outputs thereof, shown in FIGS. 2c and 2d, respectively, and having duration T equal to half the sine wave period of the oscillations from the oscillators 1 and 2, and with the repetition rate equal to the frequency of these oscillations. These pulses are inverted by the inverters 12 and 17. The output pulses from the inverters 12 and 17 are shown in FIGS. 2e and 2f, respectively. The output pulses from the shaper 11 drive the K-input of the flip-flop 18 with its J-input driven by the output pulses of the inverter 17. The output pulses from the shaper 16 are applied to the K-input of the flip-flop 13 with its J-input driven by the output pulses of the inverter 12. The pulse outputs of the flip-flops 13 and 18 are shown in FIGS. 2g and 2h, respectively. In this case, with no test sample placed inside the coil 6 of the operating oscillator 1, these pulses have the same duration T as the pulse outputs of the shapers 11 and 16. D.C. components illustrated in FIGS. 2i and 2j, respectively, are extracted out of the pulse sequences derived from the outputs of the flip-flops 13 and 18, by means of the low-pass filters 14 and 19, respectively. Since the magnitudes of these D.C. components are identical, the current through the indicator 10, which is proportional to their difference, is equal to zero. The current flow through the indicator 10 is shown in FIG. 2k.

When the coil 6 of the operating oscillator 1 receives the test sample that may be in the form of either a solid body or loose material contained in a special enclosure, the resonant circuit of the operating oscillator 1 is detuned. The oscillators 1 and 2 being mutually synchronized, the detuning of either of them results in a phase shift occurring between their oscillations, as seen on the right of the FIGS. 2a and 2b. The oscillation frequency of the oscillators 1 and 2 is not changed. The magnitude of the phase shift is given by Eq. (1). Hence the output pulses (FIG. 2c) from the pulse shaper 11 are shifted with respect to the output pulses (FIG. 2d) from the pulse shaper 16 by the amount Δt, a value proportional to the phase shift between the oscillations of the oscillators 1 and 2, which in turn results in a change of duration of the pulses at the outputs of the flip-flops 13 and 18, namely, the width of the pulses (FIG. 2g) at the output of the flip-flop 13 becomes T+Δt and the width of the pulses (FIG. 2h) at the output of the flip-flop 18 becomes T−Δt. As a consequence, the D.C. component (FIG. 2i) of the pulse sequence from the flip-flop 13 is increased, whereas the D.C. component (FIG. 2j) of the pulse sequence from the flip-flop 18 is decreased. A current (FIG. 2k) proportional to twice the phase shift between the oscillations of the oscillators 1 and 2, and consequently in proportion to the measured amount, flows through the indicator 10.

When making measurements, the switch 24 of the attenuator 23 is set so that the pointer of the indicator 10 lies in the working section of the scale. By virtue of the above selection of values of the resistors 25 through 28, the phase shift angle between the oscillators 1 and 2 will not then exceed 30° for the upper end of the respective subrange. In this case, Eq. (1) may be written as:

$$\phi = \frac{E_m}{E} KP \qquad (2)$$

with an error of no more than 2% for each measuring subrange. Hence the proposed apparatus enables the magnetic content to be measured with a total measurement error no more than 10%.

It will be understood, that the above disclosed embodiment of the invention is only presented by way of example, and various changes and modifications of the proposed apparatus are possible. In particular, some different configurations of the attenuator, as well as the phase meter, such as those with digital readout, can be used.

What is claimed is:

1. An apparatus for measuring the magnetic content of non-metallic samples, comprising:
   an operating sine wave oscillator including a resonant circuit with an inductance coil adapted to receive a test sample, said operating oscillator having an output;
   a reference sine wave oscillator including a resonant circuit having a tuning frequency equal to that of said resonant circuit of said operating oscillator, said reference oscillator having an output;
   a phase meter connected to said outputs of said operating and reference oscillators and measuring a phase shift between oscillations of said operating and reference oscillators as the test sample is placed inside said inductance coil of said resonant circuit of said operating oscillator; and
   a neutral synchronization loop for synchronizing said operating and reference oscillators, comprising a pair of inductance coils inductively coupled with said coils of the resonant circuits of said operating and reference oscillators, and a switchable resistive attenuator for varying the resistance of said mutual synchronization loop according to the magnetic content of the test sample, said switchable resistive attenuator being included between the terminals of the inductance coils not connected with a common bus, so that the phase shift between the oscillations of said operating and reference oscillators, with any amount of the magnetic material in the test sample within the specified measuring range, will not exceed 30°.

2. An apparatus for measuring the magnetic content of non-metallic samples as disclosed in claim 1, wherein said operating and reference oscillators each comprise an operational amplifier including a non-inverting input, an inverting input and an output, and a capacitor connected between said non-inverting input and said output of said operational amplifier, said resonant circuit of its associated oscillator being connected between said non-inverting and inverting inputs of said operational amplifier, said output of said operational amplifier serving as said output of the associated oscillator.

* * * * *